United States Patent [19]

Laghi et al.

[11] Patent Number: 5,728,168
[45] Date of Patent: Mar. 17, 1998

[54] ELASTOMER REINFORCEMENT OF AN ELASTOMER INTERFACE MEMBR FOR RESIDUAL LIMB OF AN AMPUTEE

[75] Inventors: Aldo A. Laghi, Clearwater; Donald R. Fox, St. Petersburg, both of Fla.

[73] Assignee: Alps South Corporation, St. Petersburg, Fla.

[21] Appl. No.: 739,376

[22] Filed: Oct. 29, 1996

[51] Int. Cl.$^6$ ............................................. A61F 2/80
[52] U.S. Cl. ................... 623/36; 623/27; 623/33; 623/37
[58] Field of Search ................. 623/27, 33, 36, 623/37

[56] References Cited

U.S. PATENT DOCUMENTS

| | | |
|---|---|---|
| 2,202,598 | 6/1940 | Petersen . |
| 2,696,011 | 12/1954 | Galdik . |
| 3,393,407 | 7/1968 | Kandel ........................... 623/37 |
| 4,479,272 | 10/1984 | Beldnisky . |
| 4,502,301 | 3/1985 | Swallow et al. . |
| 5,133,754 | 7/1992 | Laghi . |
| 5,376,132 | 12/1994 | Caspers . |
| 5,480,455 | 1/1996 | Norvell ........................... 623/36 |
| 5,503,543 | 4/1996 | Laghi ........................... 623/27 |
| 5,507,722 | 4/1996 | Richardson . |
| 5,507,834 | 4/1996 | Laghi ........................... 623/36 |
| 5,534,034 | 7/1996 | Caspers . |

FOREIGN PATENT DOCUMENTS 2620933  3/1989  France ........................... 623/36

*Primary Examiner*—Paul B. Prebilic
*Attorney, Agent, or Firm*—Joseph C. Mason, Jr.

[57] ABSTRACT

Elastomeric interface for prosthesis having two integral and inseparable sections separated by a line of demarcation where the hardness of the two sections is shown. The interface has a first soft section and a second hard section. The soft section makes contact with the skin. The hard section is located at the connection points to the prosthesis. The interface is made by injecting a first batch of soft elastomer into a mold, followed by the injection of a second batch of hard elastomer into the mold, onto the first-formed part, so that the materials of different hardness bond naturally to one another.

2 Claims, 3 Drawing Sheets

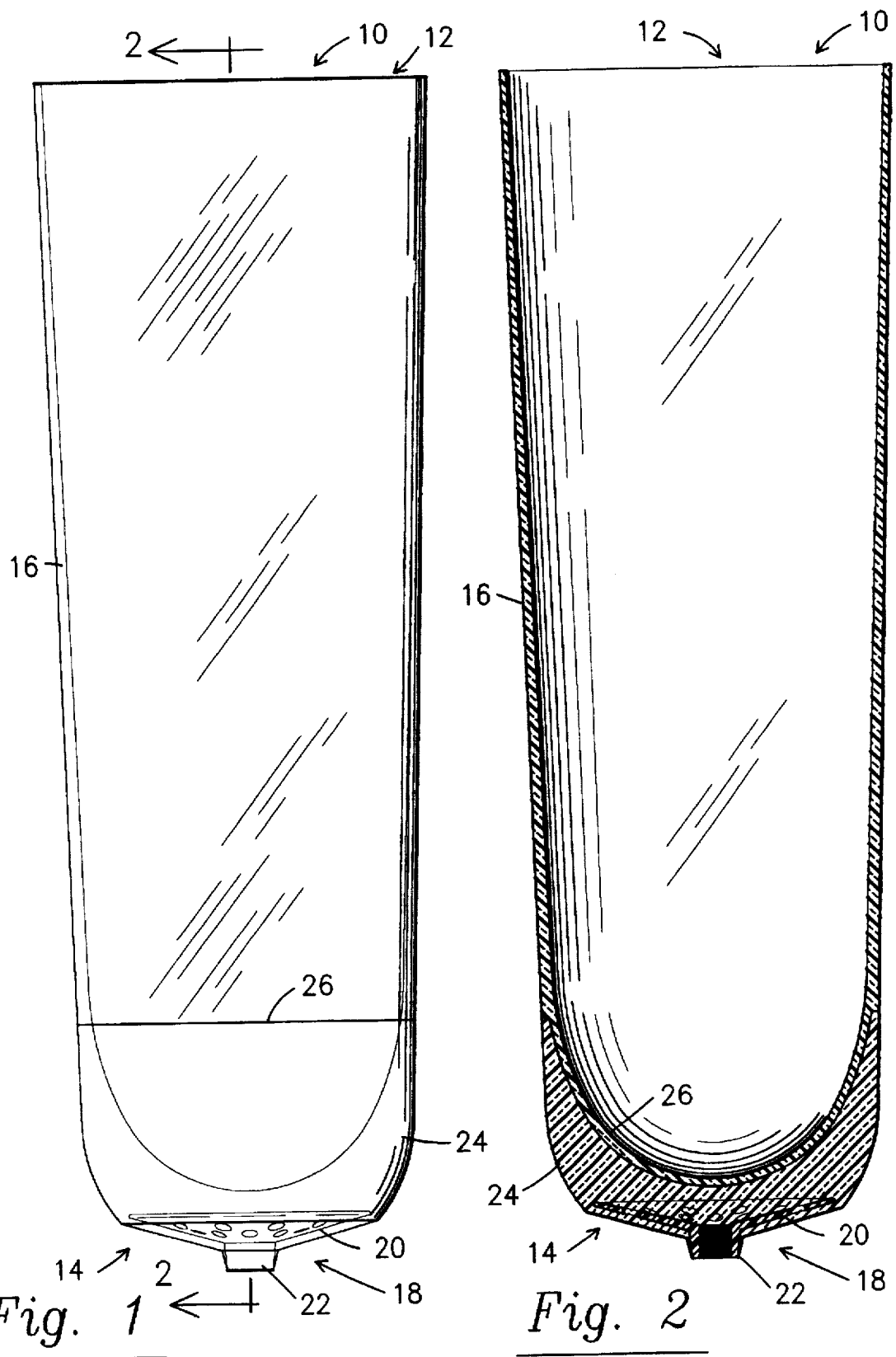

ELASTOMER REINFORCEMENT OF AN ELASTOMER INTERFACE MEMBR FOR RESIDUAL LIMB OF AN AMPUTEE

FIELD OF INVENTION

This invention relates, generally, to an elastomer reinforcement of an elastomer interface member worn upon the residual limb of an amputee, which provides additional strength and durability at the point of connection between the elastomer interface member and a prosthesis. More particularly, it relates to an elastomer reinforcement and interface member of non-uniform hardness.

BACKGROUND ART

Prosthesis sockets are hard, rigid devices that receive the residual limb, also known as the stump, of an amputee. Individuals requiring the use of such sockets typically wear several layers of socks over their residual limbs in an effort to provide a cushioning means between the stump and the socket; the socks work reasonably well as a cushioning means, but do not serve the function of holding the socket onto the residual limb.

Accordingly, several means have been developed for cushioning the residual limb and holding the socket onto the limb. For example, U.S. Pat. No. 4,923,475 to Gosthnian et. al. discloses a stump-receiving socket having a plurality of inflatable bladders, each of which includes a relatively soft, flexible membrane made of a suitable material, such as, polyurethane. The idea behind the design is to maximize the weight-bearing area while minimizing or eliminating pressure points through the judicious use of the inflatable bladders.

Most of the earlier interface members, however, lack strength and durability, as the materials used to provide the cushioning means tended to exhibit poor anti-tear properties. Thus, U.S. Pat. No. 4,923,474 to Klasson et. al. discloses a cushioning member made of an elastomeric material having a fiber embedded therein to increase its strength. However, the fabric reinforcement introduces several other problems. It concentrates stresses at the end of the fabric insert causing tears on the elastomeric materials. The fabric prevents a clear view of the residual limb while the interface is worn in those cases where a clear elastomer is used. A clear view of the distal end assists in ascertaining whether air is entrapped during placing the interface on the residual limb. If air is entrapped, the pumping action of deambulation will cause the limb to bleed. Additionally, embedding the fabric in the elastomeric material is an expensive process.

Further, these earlier elastomeric interface means share a common structural feature: the same hardness through the elastomer member's entirety.

What is required, then, is an elastomeric interface member having strength and durability derived from its formulation and not from fabrics embedded it. Such a fabric-free elastomeric interface member, having enhanced strength and durability, would enable the prosthetist to use it in high load areas, such as, to secure a connector device to the elastomeric interface member.

However, increasing the strength of an elastomer, without employing an embedded fabric, is accomplished normally by introducing higher levels of reinforcing filler. Such increases in reinforcing filler substantially increases the viscosity of the elastomer, and high viscosity elastomer will not properly fill a thin membrane mold used for making such prosthesis liners. Thus, a different method must be found for increasing the tear strength of the liner without substantially increasing its viscosity. The present invention provides such a method.

However, in view of the state of the art at the time the present invention was made, it was not obvious to those of ordinary skill in this art how such a reinforced elastomer interface member could be provided.

SUMMARY OF THE INVENTION

The reinforced interface member of this invention is made of a dual hardness elastomer. It allows the prosthetist to attach the interface member directly to the prosthesis using embedded connector parts. It is adaptable for the proximal or distal attached prosthesis.

More specifically, it is an apparatus worn on a residual limb to serve as an interface between the residual limb and a prosthesis, comprising: a first section made of a preselected elastomer material having a first predetermined hardness accurately conforming to the shape of the residual limb; the first predetermined hardness being a Shore A hardness substantially between five and twenty; the second section at the distal end, made of the preselected elastomer material having a second predetermined hardness different from the first predetermined hardness; and the second predetermined hardness being a Shore A hardness substantially between thirty and eighty. The preselected elastomer material can be made of a clear silicone rubber.

The result is an interface member which has a soft and flexible inner surface, and a firm, and tear-resistant outer section at the point of connection to the prosthesis device. The flexibility of the inner surface of the interface member helps to improve circulation, and substantially eliminates noticeable shear and friction forces against the skin. The stiffness of the outer section at the distal end results in a reduction of pistoning in patients with great amounts of redundant tissue at the distal end of their residual limbs.

Importantly, the ability to embed the connection insert into the harder, outer section of the interface member ensures that the insert and interface member will not separate from one another and that the connection insert can be placed anywhere on the interface member, so that it can be used for all types of prosthesis devices.

These and other important objects, features and advantages of the invention will become apparent as this description proceeds.

The invention accordingly comprises the features of construction, combination of elements and arrangement of parts that will be exemplified in the described construction, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a front elevational view of a socket-limb interface;

FIG. 2 is a longitudinal sectional view thereof;

DETAILED DESCRIPTION OF THE INVENTION

Figure 3:
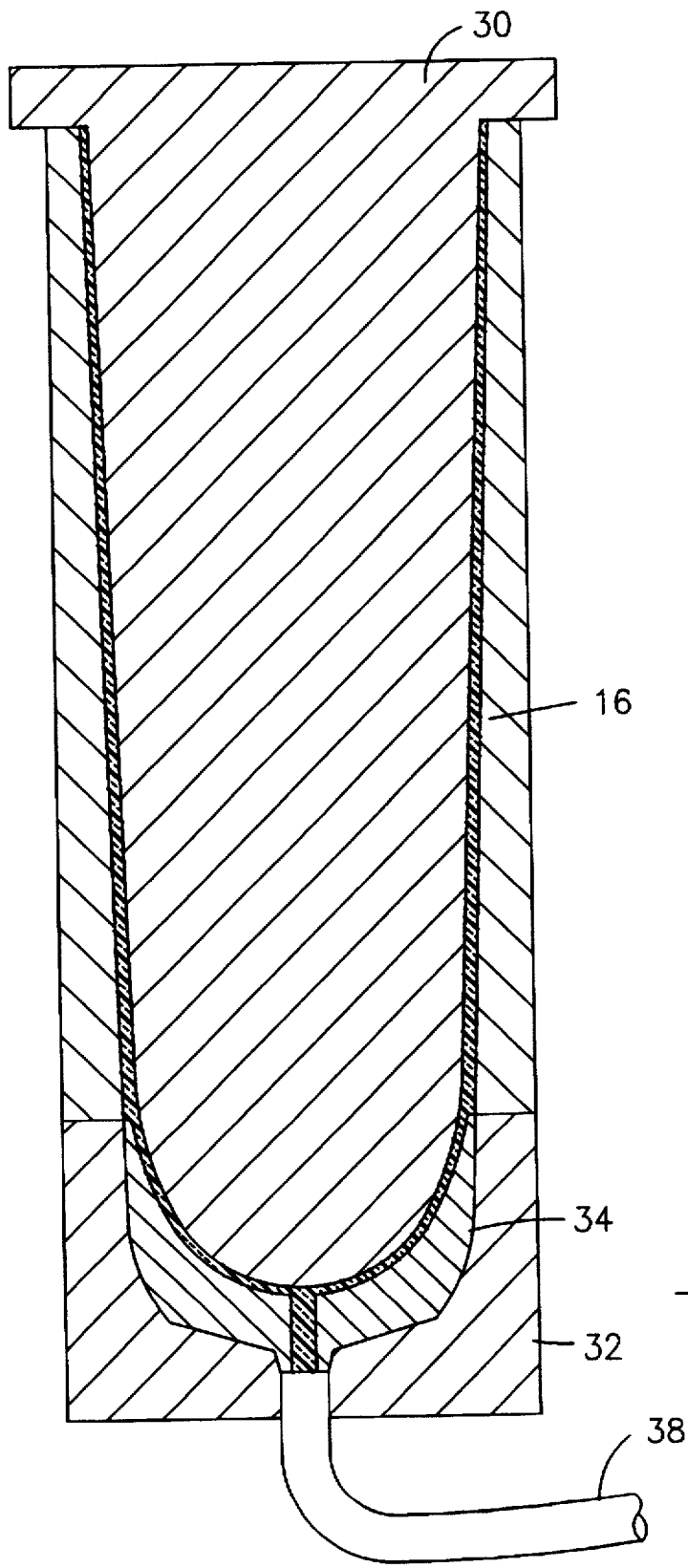
FIG. 3 is a longitudinal sectional view of an interface mold with configuration insert.

Referring now to FIGS. 1 and 2, it will there be seen that an exemplary embodiment of the invention is denoted as a whole by reference numeral 10. However, the invention is not limited to distal connection or socket-type prosthesis devices.

The reinforced interface member 10 has an open upper end 12 for receiving a residual limb, not shown, a closed bottom end 14, and sidewalls 16 of predetermined thickness and hardness. The member 10 has two integrally formed sections; upper and innermost section 16 has a first predetermined hardness, and lower and outermost section 24 has a second predetermined hardness. Arcuate line 26 is the line of demarcation between sections 16 and 24, but it should be understood from the outset that said line does not represent a parting line and that the method of making device 10, as set forth hereinafter, produces a device of unitary construction. More specifically, the softer rubber of section 16 has a slightly different appearance than the harder rubber of section 24, and the purpose of line 26 is simply to point out said difference in appearance. No difference in appearance is readily visible under casual inspection of interface member 10.

The preferred thickness of the sidewalls is about 3.0 mm. Note that the thickness is greater at the bottom end than in the sidewalls; the preferred thickness of the silicone at said bottom end is about 12.0 mm.

A nonsilicone insert member 18, shown in FIGS. 1 and 2 is partially embedded within section 24 at the bottom end of the interface. More particularly, base 20 of insert member 18 is embedded within said thickened elastomer, and internally threaded boss part 22 thereof is screw threadedly engageable to an externally threaded screw (not shown) that projects upwardly from the socket to prevent unwanted separation of the socket and interface.

In a contemplated commercial embodiment of the present invention, section 16 has a Shore A hardness rating between five to twenty and section 24 has a Shore A hardness rating between thirty to eighty. Thus, section 16, which is in contact with the skin of the residual limb, is soft; this is desirable because such softness facilitates its positioning relative to the limb. Section 24, however, is firm; this is desirable because at the connection point to the prosthesis such firmness facilitates securing the prosthesis to the residual limb.

Demarcation line 26 is visible, but the two sections of the member 10 are integrally formed and inseparable from one another.

The method for making the novel reinforced interface member 10 will now be disclosed.

Figure 4:
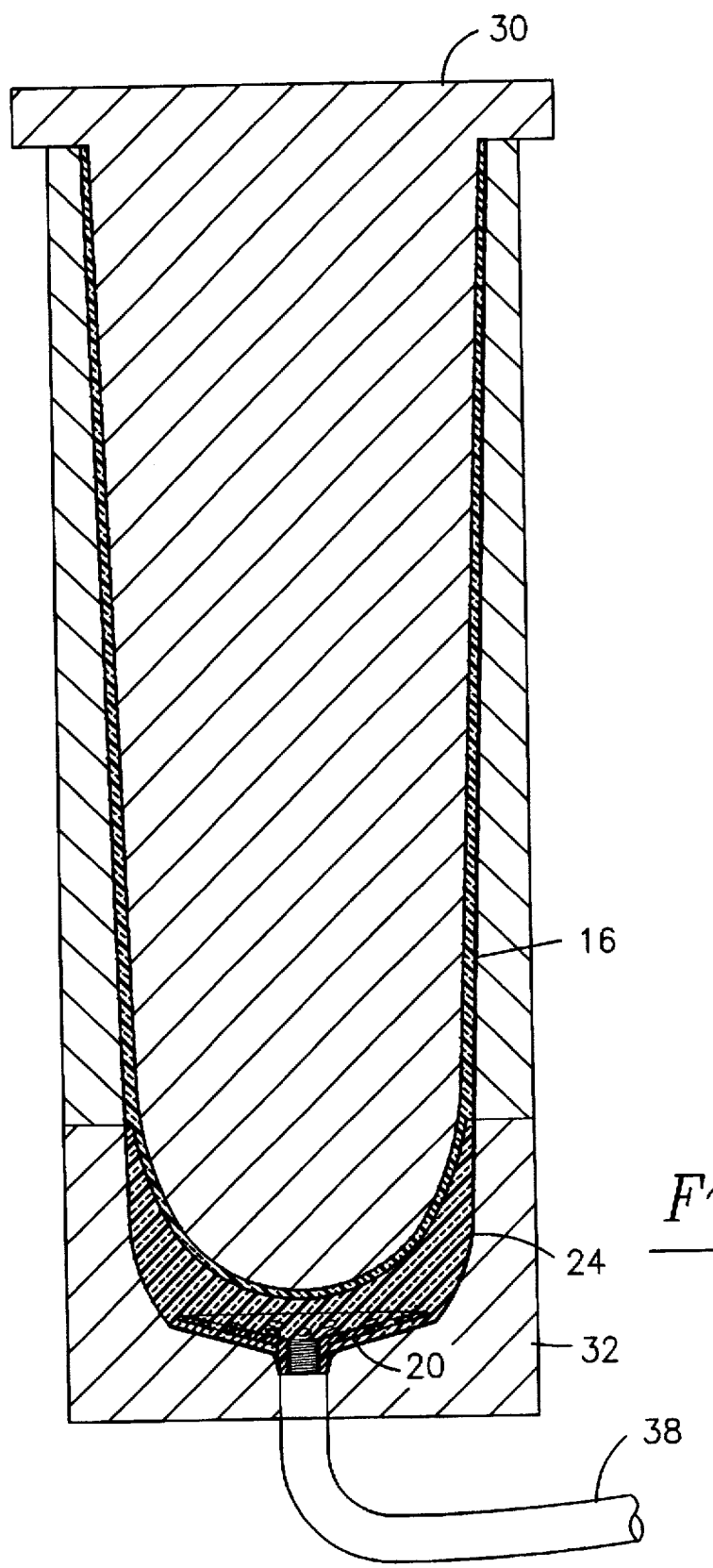
FIG. 4 is a longitundinal sectional view of an interface mold with dual hardness elastomeric interface member and nonsilicone insert.

As shown in FIG. 3, the elastomer having a first preselected hardness is first injected through injection means 38 into a mold 30 with a configuration insert 34 to form the first section 16 of the interface member. In FIG. 4, the configuration insert 34 is removed by removing a lower part 32 of the mold 30 and extracting the configuration insert 34, then the configuration insert 34 is replaced with a smaller nonelastomer insert 20 and the lower part 32 reattached to mold 30. The elastomer having a second preselected hardness 24 is thereafter injected through injection means 38 into the part of the mold which contained the configuration insert, in overlying relation to the first-injected section. By selecting the proper formulae for the two elastomer compounds, a natural bond is formed between the two sections of different hardnesses.

Significantly, no adhesives are used in the manufacturing process. The natural cohesive bond between the elastomers having differing degrees of hardness ensures that the sections will not separate from one another.

This invention is clearly new and useful. Moreover, it was not obvious to those of ordinary skill in this art at the time it was made, in view of the prior art considered as a whole in accordance with the requirements of law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also understood that the following claims are intended to cover all of the generic and specific features of the invention herein described, and all statements of the scope of the invention which as a matter of language, might be said to fall therebetween.

Now that the invention has been described,

What is claimed is:

1. An apparatus worn on a residual limb to serve as an interface between the residual limb and a prosthesis, comprising:

a first section made of a preselected elastomer material having a first predetermined hardness accurately conforming to the shape of the residual limb;

the first predetermined hardness being a Shore A hardness substantially between five and twenty;

a second section overlaying a distal portion of the first section, the second section made of the preselected elastomer material having a second predetermined hardness different from the first predetermined hardness;

the second predetermined hardness being a Shore A hardness substantially between thirty and eighty; and a nonelastomer connection member bonded to the apparatus by partial insertion in the second section, so that the apparatus can be connected to the prosthesis.

2. The apparatus of claim 1, in which:

the preselected elastomer material is a clear silicone rubber.

\* \* \* \* \*

UNITED STATES PATENT AND TRADEMARK OFFICE
CERTIFICATE OF CORRECTION

PATENT NO. : 5,728,168
DATED : March 17, 1998
INVENTOR(S) : Aldo A. Laghi, Donald R. Fox It is certified that error appears in the above-indentified patent and that said Letters Patent is hereby corrected as shown below:

On the title page and column 1, line 2, the Title should be:

ELASTOMER REINFORCEMENT OF AN ELASTOMER INTERFACE MEMBER FOR RESIDUAL LIMB OF AN AMPUTEE

Signed and Sealed this

Fourteenth Day of July, 1998

Attest:

BRUCE LEHMAN

*Attesting Officer*     *Commissioner of Patents and Trademarks*